(12) United States Patent
Al-Mulla et al.

(10) Patent No.: US 8,637,461 B2
(45) Date of Patent: Jan. 28, 2014

(54) METHOD OF DIAGNOSING AND TREATING OXIDATIVE STRESS-IMPAIRED WOUND HEALING

(75) Inventors: Fahd Al-Mulla, Al-Yarmouk (KW);
Milad Bitar, Al-Yarmouk (KW)

(73) Assignee: Kuwait University, Safat (KW)

( * ) Notice: Subject to any disclaimer, the term of this patent is extended or adjusted under 35 U.S.C. 154(b) by 2 days.

(21) Appl. No.: 13/339,333

(22) Filed: Dec. 28, 2011

(65) Prior Publication Data

US 2013/0172253 A1 Jul. 4, 2013

(51) Int. Cl.
*A61K 38/30* (2006.01)

(52) U.S. Cl.
USPC .......................................................... 514/8.5

(58) Field of Classification Search
None
See application file for complete search history.

(56) References Cited

U.S. PATENT DOCUMENTS

| | | | |
|---|---|---|---|
| 2006/0100189 A1 | 5/2006 | Gurtner et al. | |
| 2009/0220450 A1 | 9/2009 | Green et al. | |

OTHER PUBLICATIONS

Fiorentini et al. Free Radic. Biol. Med. 37(9): 1402-1411, 2004.*
Diegelmann RF et al, Frontiers in Bioscience vol. 9, pp. 283-289 (Abstract only)(2004).
Lohman R et al, Proteases and the Diabetic Foot Syndrome; Mechanisms and Therapeutic Implications. Diabetes Care, vol. 28, pp. 461-471 (2005).
Nouvong A et al, Evaluation of Diabetic Foot Ulcer Healing with hyperspectral imaging of oxyhemoglobin and deoxyhemoglobin, Diabetes Care, vol. 32 (11), pp. 2056-2061 (2009).
Pratipanawatr T et al, "Effect of IGF-1 on FFA and glucose metabolism in control and type 2 diabetic subjects", American Journal of Physiology: Endocrinology and Metabolism, vol. 282, pp. E1360-E1368 (2002).
Regan FM et al, "Treatment with recombinant human insulin-like growth factor (rhIGF)-1/rhIGF binding protein-3 complex improves metabolic control in subjects with severe insulin resistance," The Journal of Clinical Endocrinology and Metabolism, vol. 95(5), pp. 2113-2122 (2010).
Tsuboi R et al, "Co-administration of insulin-like growth factor (IGF-1) and IGF-binding protein-1 stimulates wound healing in animal models," Journal of Investigational Dermatology, vol. 104(2), pp. 199-203 (Abstract only) (1995).
Shay KP et al, "Alpha-lipoic acid as a dietary supplement: molecular mechanisms and therapeutic potential", Biochimica et Biophysica Acta, vol. 1790(10), pp. 1149-1160 (2009).
Siddle K, "Signaling by insulin and IGF receptors: supporting acts and new players," Journal of Molecular Endocrinology, vol. 47, pp. R1-R10 (2011).
Jacob RJ et al, "Metabolic effects of IGF-1 and insulin in spontaneously diabetic BB/w rats," American Journal of Physiology, vol. 260(2 Pt 1), pp. E262-E268 (1991).
Shearer JD et al, "Insulin is degraded extracellularly in wounds by insulin-degrading enzyme (EC 3.4.24.56)," Amer J Physiol Endocrinol Metab, vol. 273, pp. E657-E664, (1997).
SD Boulware et al, "Comparison of the metabolic effects of recombinant human insulin-like growth factor-1 and insulin," Journal of Clinical Investigation, vol. 93, pp. 1131-1139 (1994).
Patarrão RS et al, "A new technique to assess insulin sensitivity in humans: the rapid insulin sensitivity test (RIST)," Proceedings of the Western Pharmacology Society, vol. 50, pp. 105-109 (Abstract only) (2007).
Kamenova P, "Improvement of insulin sensitivity in patients with type 2 diabetes mellitus after oral administration of alpha-lipoic acid," Hormones (Athens), vol. 5(4), pp. 251-258 (2006).

* cited by examiner

*Primary Examiner* — Christine J Saoud
(74) *Attorney, Agent, or Firm* — Richard C. Litman

(57) ABSTRACT

The method of diagnosing and treating oxidative stress-impaired wound healing allows a practitioner to identify a subject at risk of having impaired wound healing by identifying the sensitivity of that patient to IGF-1. A finding of IGF-1 resistance, either systemically or at the site of an already existing wound, indicates an increased likelihood that the wound will have difficulty healing. In addition, identifying IGF-1 resistance by this method indicates that treatment of a wound with a combination of an antioxidant, IGF-1 and IGFBP-1 will provide optimal healing.

2 Claims, 8 Drawing Sheets

METHOD OF DIAGNOSING AND TREATING OXIDATIVE STRESS-IMPAIRED WOUND HEALING

BACKGROUND OF THE INVENTION

1. Field of the Invention

The present invention relates to the treatment of wounds, and particularly to a method of diagnosing and treating oxidative stress-impaired wound healing by testing for oxidative stress, and if present, administering effective amounts of antioxidants and/or Insulin-like Growth Factor 1 (IGF-1).

2. Description of the Related Art

Wound healing is a topic of considerable study. It involves a cycle of connective tissue matrix deposition, contraction, and epithelialization.

Several overlapping stages can be identified, and these are coordinated by a cascade of cell signaling proteins. Phases include clotting and inflammation, followed by new proliferation and differentiation of cells to fill the wound. The final phase begins by day 7 and includes remodeling of the new tissue, a process that can last for months. Under certain physiological conditions, however, wound healing is delayed, prolonged, or never reaches completion. Among the diseases that are associated with impaired wound healing are diabetes, hypercortisolemia, and chronic inflammation. Among diabetes patients alone, infected/ischemic foot ulcers are estimated to be the reason for about 25% of diabetes-related hospital visits, and precede 84% of lower extremity amputations among diabetes patients. The physiological stresses associated with such diseases as diabetes are believed to deregulate cell signaling and cytokine function at the site of the injury, resulting in improper cell behavior, including a prolonged inflammatory response and increased cell death. However, it has been thought that the final outcome of impaired wound healing can result from very different physiological processes. For example, TNF-α, which is known as a mediator of chronic inflammation, and cortisol (an anti-inflammatory agent that acts through a nuclear receptor) are transduced through different cell signaling pathways, but overabundance of either leads to chronic wounds. The inventors, however, have determined that a common mechanism shared by various types of delayed wound healing is an overabundance of reactive oxygen species (ROS). In diabetes, for example, the hyperglycemic state causes nutritional imbalance among cells at the site of the injury, and also causes oxidative stress. Normal tissue responds to ROS by expressing anti-oxidative stress proteins, such as glutathione, and enzymes that repair chemical damage caused by oxidation, but this response is impaired in the diabetic state.

The role of IGF-1 in diabetes and oxidative stress has been previously studied. IGF-1 is known to improve glucose disposal in humans. IGF-1 is also known to be a wound healing agent. In fact, the combination of IGF-1 and its binding proteins has been shown to accelerate wound healing in diabetic mice.

The role of antioxidants in treating the symptoms of diabetes has also been explored. For example, lipoic acid is known in the art to be useful for treating diabetes symptoms, such as retinopathy and neuropathy IGF-1 shares partial sequence homology to insulin and is known to some degree to stimulate the same cellular receptors, and, as mentioned above, is also known to improve glucose handling in insulin-insensitive patients. However the biology of IGF-1 is incompletely understood. The tissue distribution of insulin action versus IGF-1 action is only partially overlapping. Although common intracellular signaling proteins are shared, the signaling outputs of insulin and IGF-1 differ in observable ways. For example, insulin may emphasize metabolic responses, while IGF-1 emphasizes mitogenic responses. It has been demonstrated that in particular situations and in particular tissues, insulin and IGF-1 action are not identical. Additionally insulin's role in wound repair has not been clearly delineated, whereas IGF-1 is critical.

Thus, a method of diagnosing and treating oxidative stress-impaired wound healing solving the aforementioned problems is desired.

SUMMARY OF THE INVENTION

The current invention is a method of predicting wound healing properties. The inventors have found that IGF-1 resistance, that is the inability for IGF-1 to stimulate glucose uptake and/or disposal in a patient to a normal or adequate level, is predictive that wounds suffered by that patient will not heal as quickly as wounds of patients who do not exhibit IGF-1 resistance. Furthermore, a determination that a patient suffers IGF-1 resistance is predictive that a specific therapy will be more efficacious. In a situation in which IGF-1 resistance is not detected, then an antioxidant will not be as effective. In particular, a finding of IGF-1 resistance in a patient calls for administration of an antioxidant in combination with IGF-1 and IGFBP-1. IGF-1 resistance can be assessed by one of a number of methods already established for testing insulin resistance. Numerous such tests have been previously developed; the only requirement is that the test includes the administration to a patient of an amount of IGF-1 that is expected to modulate that patient's glucose handling. For example, it is expected from previous literature that a physiologically effective dose of IGF-1 will cause the patient's body to metabolize glucose at a faster rate than without the administered dose, and that patients suffering from IGF-1 resistance will exhibit a lower increase in glucose metabolism in response to a dose of IGF-1 than patients who do not suffer from IGF-1 resistance.

Because it was not previously known that a common thread in impaired wound healing is loss of sensitivity to IGF-1, it would not have been obvious to test for IGF-1 resistance before deciding on a course of treatment that includes an antioxidant administered in conjunction with an IGF-1 and IGFBP-1 combination.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
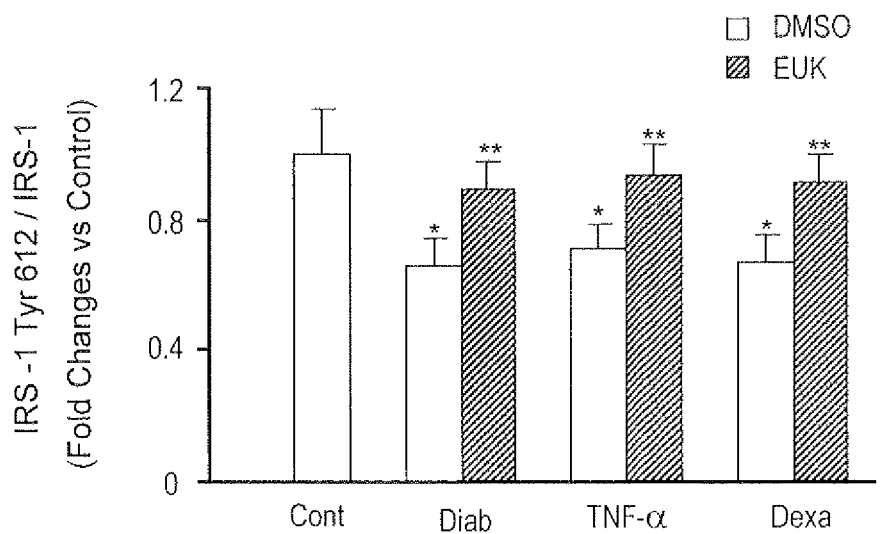
FIG. 1A is a chart showing that IGF-1 induces rapid phosphorylation of Tyr612 on IRS-1, a hallmark of receptor activation, in control fibroblasts and that this phosphorylation is diminished in diabetic fibroblasts or normal fibroblasts exposed to TNF-α or dexamethasone, and that EUK-134 ameliorates the inhibition of IRS-1 phosphorylation caused by these conditions.

The method diagnoses the risk of a subject of having difficulty with proper wound healing by observing whether the subject has decreased sensitivity to insulin-like growth factor 1 (IGF-1). In particular, if a subject displays resistance to IGF-1, then any wounds the subject suffers can be treated in a different manner than if he or she did not display IGF-1 resistance. In particular, determination that a subject has decreased IGF-1 sensitivity dictates that his or her wounds should be treated with a combination comprising an antioxidant, IGF-1 and IGFBP-1. In particular the antioxidant EUK-134 or the antioxidant α-lipoic acid can be effective as part of the treatment of wounds that have been suffered by individuals with impaired IGF-1 sensitivity.

Means for determining IGF-1 resistance can be provided by a number of assays. Many of these assays are typically used to administer insulin and monitor the body's response to it; in the case of the instant invention, the insulin is always substituted with IGF-1. Assays include, but are not limited to, hyperinsulinemic-euglycemic clamp technique, frequently sampled IV glucose tolerance test (FSIVGTT), insulin tolerance test (ITT), insulin sensitivity test (IST), and RIST (a Rapid Insulin Sensitivity Test replacing insulin with IGF-1). These tests are familiar to those practiced in the art. These assays for measuring systemic IGF-1 sensitivity (or lack thereof) involve measuring IGF-1's impact on the body through sampling the level of glucose in a subject's blood. In response to a large injected dose of IGF-1, the body of a healthy subject will absorb/metabolize an increased amount of glucose. By also injecting glucose into the blood, and measuring how much glucose is required to stabilize the subject's blood glucose concentration, a practitioner can determine a subject's sensitivity to IGF-1. As mentioned, measurement of IGF-1 resistance is not limited to the tests listed above; any test that has the potential to observably measure a test subject's body's response to a dose of IGF-1 is suitable within the context of this invention. The test must only be able to indicate IGF-1 resistance in a subject, i.e. that a subject responds to a dose of IGF-1 in a manner that is appropriate to a lesser dose of IGF-1.

Blood glucose metabolism has been studied previously in response to IGF-1 administration. For example S D Boulware et al ("Comparison of the metabolic effects of recombinant human insulin-like growth factor-1 and insulin," J Clin Invest, Vol. 93, pp. 1131-1139 (1994)) measured glucose metabolism in healthy adults at a steady IGF-1 infusion rate between 0 (i.e. basal) and 0.8 µg/kg-min. Pratipaniwatr et al (2002) measured glucose metabolism in healthy and diabetic adults in response to continuous IGF-1 infusion at 26 pmol/kg-min and 52 pmol/kg-min; they noted IGF-1 resistance in diabetic subjects in addition to insulin resistance. Diabetic patients showed virtually no response to IGF-1 at 26 pmol continuous infusion, whereas they showed about a 40% decrease to IGF-1 at 52 pmol continuous infusion relative to healthy adults. While the two studies above relied on a continuous infusion of IGF-1 during the assay period, it is also possible to inject a single bolus of IGF-1, which is the protocol of a Rapid Insulin Sensitivity Test for example (see, e.g., Patarrão R S et al, 2007). These methods of determining IGF-1 resistance have established standards for a healthy response to IGF-1 administration in humans (see, e.g., Pratipatawanr T et al, "Effect of IGF-1 on FFA and glucose metabolism in control and type 2 diabetic subjects," American Journal of Physiology—Endocrinology and Metabolism, Vol. 282, pp. E1360-E1368 (2002)).

Antioxidants such as α-lipoic acid also have an effect on glucose metabolism in humans; for example they are known to improve insulin sensitivity in diabetics. Evidence has also accumulated in data collected from humans and other mammals, however, that antioxidants do not change the glucose sensitivity of healthy patients: therefore such antioxidants return patients to normal rather than generally boosting glucose metabolism irrespective of health or disease (see, e.g., Kainenova, 2006). Antioxidants such as α-lipoic acid or EUK-134 can be administered intravenously or orally in a method of determining IGF-1 resistance.

Antioxidants can also be administered in an acute intravenous dose in the method of this invention. If a patient who appears to have some level of IGF-1 insensitivity responds to an acute dose of intravenous α-lipoic acid, for example, then the practitioner of the current invention can assume that a disease of IGF-1 resistance is present and that a course of IGF-1 and IGFBP-1 therapy for a wound should include an antioxidant such as, but not limited to, α-lipoic acid or EUK-134. In the case of α-lipoic acid, an acute intravenous dose for initially determining IGF-1 resistance is preferably between about 500 mg and about 2000 mg. IGF-1 resistance can also be determined through chronic administration of α-lipoic acid, either orally or intravenously. The chronic course of therapy can be continued for anywhere between 2 days and greater than 3 months; these protocols are well-known to those of skill in the art. The dose of α-lipoic acid to be taken orally can range anywhere between 1 mg per day and 3000 mg per day for a human; these doses are effective for both determining IGF-1 resistance and for combination therapy in the event a subject suffering IGF-1 resistance incurs a wound. Preferably the dose is between about 100 mg per day and 1000 mg per day. In the method of determining IGF-1 resistance, the practitioner would monitor the patient's IGF-1 sensitivity at any point between 2 days and greater than 3 months after initiating the antioxidant regimen. The practitioner may only require a single IGF-1 resistance test during the course of the chronic dosing regimen, or the practitioner may repeat the IGF-1 resistance test a plurality of times after beginning antioxidant therapy, or may even repeat the entire IGF-1 resistance test a plurality of times. These matters are within the judgment of one of ordinary skill in the biomedical arts.

Alternatively a practitioner may diagnose IGF-1 resistance by ascertaining the state of IGF-1 signaling at the site of the wound. IGF-1 resistance can be assayed at the site of the wound by biopsy of enough cells to measure phosphorylation status of intracellular transducers of IGF-1 with assays known in the art. Such assays include, but are not limited to, western-blotting, ELISA, and cell-based ELISA. Any assay that can measurably detect protein phosphorylation is suitable within the context of this invention.

IGF-1 initiates a cascade of signaling inside the cells at the site of a wound, and these signaling cascades promote the healing of the wound. The cells sampled to determine IGF-1 resistance may be taken from directly within the wound or they may come from tissue in the immediate vicinity of the wound. Among the intracellular proteins that mediate the IGF-1 signaling are Insulin Receptor substrate-1 (IRS-1), Jun N-terminal kinase (JNK), Akt, and PI3 kinase (PI3K). These proteins are able to amplify or inhibit the IGF-1 signal depending on whether, and where, they have been phosphorylated. For example IRS-1 can be phosphorylated on a tyrosine at position 612, which activates the IGF-1 signal, or it can be phosphorylated on a serine at position 307, which will inhibit the IGF-1 signal. Measurement of the phosphorylation status and location of the above transducers of the IGF-1 signal will indicate how readily cells will respond to exposure to IGF-1. Therefore determination of the phosphorylation status of these intracellular proteins in and around the wound are also indicative of "IGF-1 resistance"; and like the IGF-1 resistance that can be measured systemically through a glucose metabolism test, the IGF-1 resistance encountered in cells in and around the site of the wound can be counteracted by antioxidants such as EUK-134 and α-lipoic acid. In determining whether these proteins are responsive to antioxidants, the cells can be removed from the vicinity of the wound and then exposed to antioxidant, i.e. in vitro treatment with antioxidant. Alternatively, cells can be removed from the vicinity of the subject's wound, the phosphorylation/activation status can be determined, then the subject can be treated with antioxidant and further cells can be removed to identify changes in the phosphorylation/activity levels, i.e. in response to in vivo treatment with antioxidant.

Upon determination that a subject with a wound exhibits IGF-1 resistance, therapeutic amounts of antioxidant, IGF-1 and IGFBP1 can be administered. Therapeutic amounts of IGF-1 and IGFBP-1 range from 0.1 to 1.0 mg/kg given intravenously (see e.g. Regan F M et al, "Treatment with recombinant human insulin-like growth factor (rhIGF)-1/rhIGF Binding Protein-3 complex improves metabolic control in subjects with severe insulin resistance," J Clin Endocrinol Metab, Vol. 95(5), pp. 2113-2122 (2010)). Topically, concentrations of IGF-1 and IGFBP-1 each can range from 0.1 to 50 µg per ml; the preferred ratio of IGF-1 to IGFBP-1 by mass can range from 10:1 to 1:10. These proteins can be included with any pharmaceutically acceptable carrier or excipient.

The following examples are put forth so as to provide those of ordinary skill in the art with a complete disclosure and description of how to apply the disclosed method, and are not intended to limit the scope of what the inventors regard as their invention. The following materials and methods were followed in each of the following Examples 1 through 6, where applicable.

Primary dermal fibroblasts were obtained from dorsal skin of female Goto Kakizaki (GK, age 12-15 months) rats, a model for non-obese type 2 diabetes, and their Wistar control counterparts. After sterilization in povidine solution, rat skin was washed in sterile water and rinsed in 70% ethanol in PBS. Epidermis and dermis were separated following overnight incubation in 0.25% trypsine/EDTA at 4 C. Dermis was cut into small pieces and incubated in Dulbecco's modified Eagle medium (DMEM; Invitrogen) containing collagenase (250 U/ml; Sigma) for thirty min at 37 C in 5% $CO_2$ with constant agitation. The sections were triturated vigorously to release fibroblasts, which were collected by centrifugation. The cell pellet was washed two times with PBS, re-suspended in complete medium (DMEM supplemented with 10% fetal calf serum, penicillin (100 U/ml), streptomycin (100 µg/ml)), 2 mM L-glutamine and 10 mM HEPES) and then cultured under a standard condition.

A hypercortisolemic state was mimicked by exposing control fibroblasts to dexamethasone (Dexa, Sigma) administered at 20 ng/ml every other day for a duration of 8 days. Similarly, the state of low-grade inflammation in fibroblasts was recapitulated experimentally by exposing these cells to TNF-α (4 ng/ml every day for 4 days). EUK (Cayman) and LA (Sigma) were most effective in cultured fibroblasts at 100 µM and 500 µM, respectively, doses that appear to have a minimum effect on cell viability as determined by the WST-based technique (Roche Diagnostics). The concentration of IGF-1 (50 ng/ml, Peprotech) was determined by prior dose response experiment.

Levels/activities of key intracellular molecules in the IGF-1 signaling cascade including IRS-1, IRS-1 Tyr-p-612, PI3K-p85α, IRS-1 Ser-p (307), PI3K, Akt, p-Akt, JNK and p-JNK were assessed using western blotting/immunoprecipitation and commercially available ELISA-based assays.

Ice-cold radioimmunoprecipitation assay (RIPA) buffer was used for the extraction of proteins from fibroblasts. Immunoprecipitation was achieved by incubating cell homogenates with anti-IRS-1 antibody overnight at 4° C. followed by the addition of protein A/G-Agarose for additional two hours. Immunoprecipitates were separated using spin-collection filters (Cytosignal), washed once with RIPA buffer/3× with PBS and then eluated by the addition of Laemmli buffer. Immunoblotting was conducted by loading equal amount of proteins (BCA protein assay kit, Pierce) on a standard 6% or 10% SDS-PAGE and the resolved proteins were transferred to a nitrocellulose membrane; membranes were blocked (1× Tris-buffered saline, 0.1% Tween 20, and 5% nonfat dry milk), incubated overnight, at 4° C. with primary antibodies (IRS-1, IRS-1 Tyr-612, IRS-1 Ser 307, PI3K-p85α Akt, p-Akt, all from Cell Signaling) and then reacted with horseradish peroxidase-conjugated secondary antibodies (1 hr, room temperature). Antigen-antibody complexes were visualized by an enhanced chemiluminescence system on BioMax Light Film (Kodack) and then the densitometry was analyzed using Quantity One 1-D image software (BioRad, GS 800). All densitometry data were corrected for equal loading using the house keeping gene β-actin and they were expressed as fold change vs. control.

PI3K activity was measured using PI3K ELISA (Echelon Biosciences Inc). This kit was used in connection with anti-p85 PI3K antibody, and it measures class IA PI3K activity as a conversion of PI(3,4,5)P2 into PI(3,4,5)P3. Briefly, cells were washed with buffer A, lysed using buffer A containing 1% NP40 and protease inhibitors, incubated on ice for 30 min and then centrifuged at 14,000×g. Following the step of immunoprecipitation of the supernatants with anti-p85 PI3K antibody and protein A-agarose beads, the kinase reaction was carried out according to the specifications provided by the manufacturers.

Activation of Akt and JNK was analyzed in fixed fibroblasts using FACE-Akt and FACE-JNK (both from Active Motife). Antibodies recognizing phosphorylated Akt (p-Ser 373) and dually phosphorylated JNK (Thr-183/Tyr-185) or total Akt and JNK were used according to the manufacturer's instructions. Briefly, cells were seeded at a density of 50,000/well in a 96-well plate and the next day the adherent cells were serum starved for 24 hr. Cells were rinsed in PBS and fixed in 3.7% PFA solution for 20 min at room temperature. Labeling with antibodies was conducted according to the manufacturer's protocol and the resulting phosphoantibody signal was calculated after correction for number of cells and total Akt or JNK levels in each sample. The results are shown as -fold change compared to control normal fibroblasts.

ROS generation in cultured fibroblasts was evaluated using dichloroflurescein-diacetate (DCF-DA, Molecular Probes), a probe that is oxidized to the fluorescent product DCF upon exposure to hydrogen peroxide, peroxynitrite, hydroxyl radical and nitric oxide. Its concentration serves as an indicator of the overall degree of intracellular oxidative stress.

Cells seeded in 96-well plates were incubated for thirty minutes at 37 C in serum free media containing 5 µM of DCF-DA. The plates were then washed twice with Krebs Ringer Buffer (KR) and the fluorescence readings were taken every 15 min for 1 hr at Ex=485 and Em=530. Subtracted background values were obtained from wells containing DCF-DA without cells. All the values of ROS were normalized to the total number of cells using PI-based assay.

Protein-bound carbonyl levels in fibroblasts, a marker of cumulative oxidative stress, were determined using a procedure in which a sensitive ELISA-based assay was used to measure total protein-bound carbonyls using oxidized bovine serum albumin (BSA) as standard. Protein samples were adjusted to 5 mg/ml and then incubated with 10 mM 2,4-dinitro-phenylhydrazine (DNP) in 6 M guanidine-HCl. DNP-derivatized proteins were adsorbed to 96-well immunoplates, incubated with primary biotinylated anti-DNP antibody, washed, reacted with streptavidine-biotinylated horseradish peroxidase and then the developed color was measured spectrophotometrically.

The proliferation and collagen synthesis of cultured fibroblasts were determined using, respectively the 5-bromo-2-deoxyuridine (BrdU) incorporation into DNA and a radiolabelled proline uptake assay.

Cells were seeded into 96-microtiter plates at a concentration of $1.5 \times 10^4$ and allowed to adhere overnight in DMEM supplemented with 10% FCS. After arrest by incubation in DMEM supplemented with 0.5% FCS for 24 hrs, cells were exposed to IGF-I (50 ng/ml) in DMEM containing 10 mM 5-bromo-2-deoxyuridine (BrdUrd). Incorporation of BrdUrd into DNA was estimated using 5-bromo-2-deoxyuridine labeling and detection kit (Roche Applied Science) according to the manufacturer's instructions.

A radiolabel proline uptake assay was used in the quantification of the rate of collagen synthesis in cultured fibroblasts derived from various experimental groups. Briefly, a confluent fibroblast monolayer was prepared in a 24-well plate and cultured overnight in media supplemented with 10 mM HEPES, 0.1% serum, 2 mM L-proline and 50 µg/ml ascorbic acid. Thereafter, the media was replaced with a fresh media containing 5 µCi/ml $^3$H L-proline (New England Nuclear) and IGF-I (50 ng/ml) and the incubation continues for 24 hrs. Synthesis of collagen and non-collagen protein was expressed, respectively as collagenase-soluble and collagenase insoluble count per minute. A correction factor of 5.4 for non-collagen protein was used to adjust for the relative abundance of proline and hydroxyproline in collagen.

For in vitro wounding (migration) experiments, cultured fibroblasts were grown in six well plates until they reached confluence. Medium was removed, and cells were rinsed and then cultured for 24 h in serum-free medium plus 0.1% BSA. The monolayer was artificially injured by scratching across the plate with a pipette tip, washed to remove detached cells and then cultured in serum free medium in the presence of mitomyocin C (10 µg/ml, to prevent cell proliferation). After 24 h, images of the scratched area under various experimental conditions were photographed. Scratch wound area was measured and the percentage of wound closure was measured according to the following formula: (1−[current wound size/initial wound size)]×100.

All animal procedures were performed in accordance with the NIH Guidance for the Care and Use of Laboratory Animals. The current study used, respectively the GK and Dexamethasone-treated rats as models for diabetes and hypercortisolemia. Dexamethasone was administered subcutaneously at a dose of 2.5 µg/kg body weight in the morning (8:00 AM) and in the evening (8:00 PM) for a duration of four weeks before wounding and this form of therapy continued during the course of healing. Preliminary studies involving a concentration-dependent curve revealed that the aforementioned dose of dexamethasone chosen was effective in inducing IGF-1 resistance and also in impairing the healing process without a significant effect on body weight. Weight and age-matched female Wistar rats (Kuwait University breeding colony) served as the corresponding controls. All of the animals were maintained under standard conditions with 12 hours on/off light cycle, commercial diet, and water ad libitum. GK rats destined for wounding were initially matched with regard to body weight (e.g., 230 to 250 g), and plasma levels of glucose, free fatty acids and insulin. These indices are commonly used to reflect the severity of the diabetic state.

Animals used for IGF-1 sensitivity (n=6/group) and wound healing (n=8) studies were partitioned into five study groups including control, diabetic, hypercortisolemic, diabetic+EUK and hypercortisolemic+EUK. The EUK-134 was administered for duration of four weeks before wound induction and it continued during the course of healing. EUK-134 at a dose of 12.5 mg/kg body weight was administered intraperitoneally (ip) every other day before and during the wound healing studies; α-lipoic acid (LA), an ROS scavenger/anti-oxidant enzyme inducer, was alternatively administered at a dose of 50 mg/kg body weight/day.

IGF-1 sensitivity in control, diabetic and hypercortisolemic animals was determined using the rapid insulin sensitivity test (RIST) with IGF-1 (200 µg/kg BW) infused instead of insulin. The RIST index is the amount of glucose per kg body weight required to maintain euglycemia following a bolus of insulin (50 mU/kg BW).

Animals derived from various experimental groups were anesthetized by ip, injection of 90 mg ketamine+10 mg xylazine/kg body weight, and their back skin was shaved, depilated with Nair and cleaned with 70% alcohol. Six bilateral full-thickness excisional wounds (8 mm in diameter) at equidistant from midline were created on the dorso-rostral back skin. Wounds were separated by a minimum of 1 cm of uninjured skin. The IGF-I therapeutic regimen included a combination of IGF-I and IGFBP-1 (5 µg IGF-I and 1.5 µg IGFBP-1) which was applied every other day to the wound in a vehicle of pluronic acid in phosphate buffered saline solution (300 mg/ml, 250 µl total volume per wound). Wounds were photographed at 0 and 7 days after wounding using a Sony D-9 digital camera. The wound area was analyzed using Adobe PhotoShop (version 7.0; Adobe Systems) and the percentage of wound closure was derived by the following formula: (1−[current wound size/initial wound size])×100.

Data are expressed as the mean±SEM. One-way analysis of variance with Bonferroni post hock validation or the Mann-Whitney test was used to compare data derived from various experimental groups. A level of $P \leq 0.05$ was considered to be significant.

Example 1

Figure 1B:
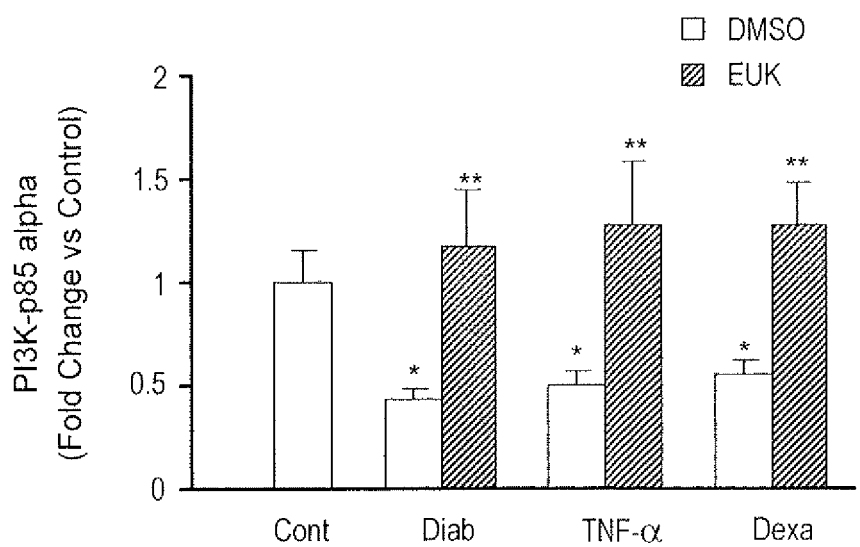
FIG. 1B is a chart showing that IGF-1 activates PI3K; the active subunit of PI3K (p85α) is co-precipitated with IRS-1 in response to IGF-1 exposure, however this association is diminished in diabetic, TNF-α-, or dexamethasone-exposed fibroblasts, and that EUK-134 restores this association.
Figure 1C:
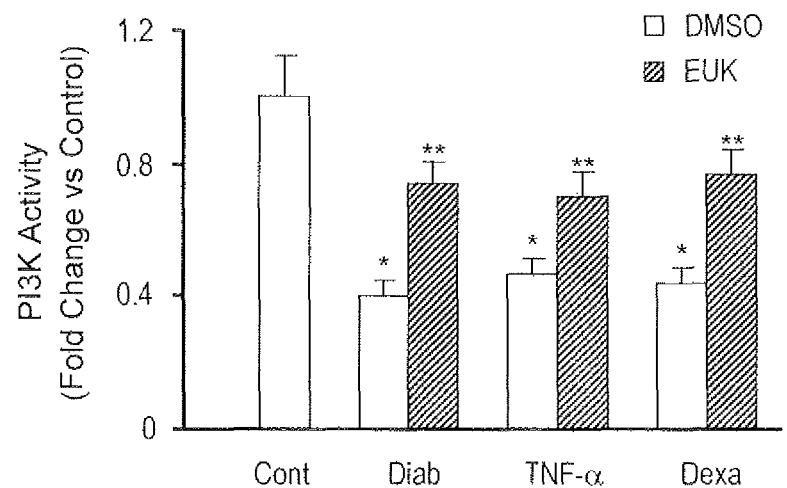
FIG. 1C is a chart showing a kinase assay measuring actual enzymatic activity of PI3K. IGF-1 increases PI3K enzymatic activity, whereas a diabetic state, TNF-α exposure, or dexamethasone exposure, diminish activity. This activity is partially restored by co-exposure of the cells to EUK-134.
Figure 1D:
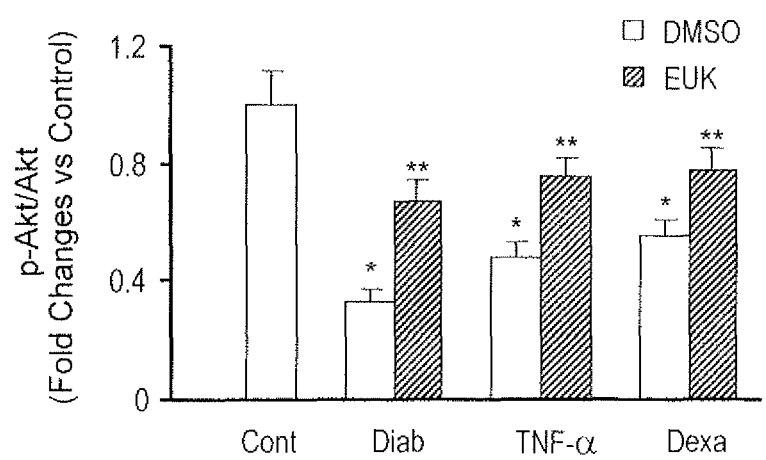
FIG. 1D is a chart showing that Akt, a target of PI3K, is phosphorylated (activated) in normal fibroblasts by exposing them to IGF-1, but that this response is diminished in diabetic, TNF-α-, or dexamethasone-exposed cells; Akt phosphorylation is partially restored by EUK-134.
Figure 1E:
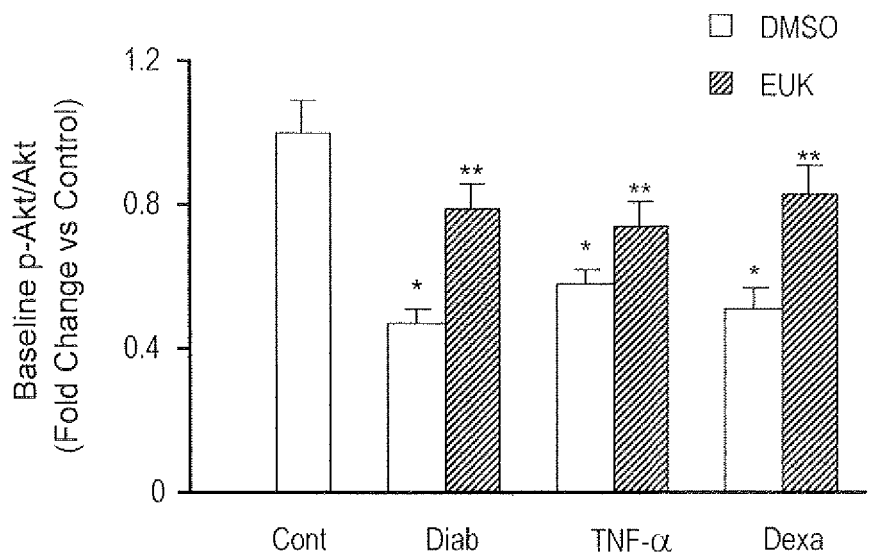
FIG. 1E is a chart of ELISA (an alternative assay method) results showing that Akt, a target of PI3K, is phosphorylated (activated) in normal fibroblasts by exposing them to IGF-1, but that this response is diminished in diabetic, TNF-α-, or dexamethasone-exposed cells, and that Akt phosphorylation is partially restored by EUK-134.

Example 1 represents a study of impaired IGF-1-induced activation of the PI3K/Akt pathway in fibroblasts with phenotypic features of diabetes and hypercortisolemia. Key intracellular molecules within the IGF-1 signaling pathway in fibroblasts, one of the major target cells of IGF-1 during wound healing, were analyzed using immunoprecipitation/western blotting and ELISA-based techniques. In control fibroblasts, 50 ng/ml IGF-I induced rapid and strong activation of IRS-1, as evidenced by the phosphorylation of Tyr-612, an essential element for IRS-1 activation and the generation of a docking site for the downstream PI3K (FIG. 1A). IGF-1 also increased the activity of PI3K and promoted the phosphorylation of Akt at Ser-473 in these cells (FIG. 1B-D). In contrast, this sequence of events is impaired in fibroblasts with phenotypic features of diabetes and hypercortisolemia (FIG. 1A-D). Because baseline levels of p-Akt or p-JNK were not reproducibly detectable using western blotting, a Fast Activated Cell-based (FAC) ELISA kit (Active Motif) was applied with the resulting data documenting a significant decrease in p-Akt/Akt ratio in the aforementioned disease-based models of fibroblasts (FIG. 1E).

Example 2

Figure 2A:
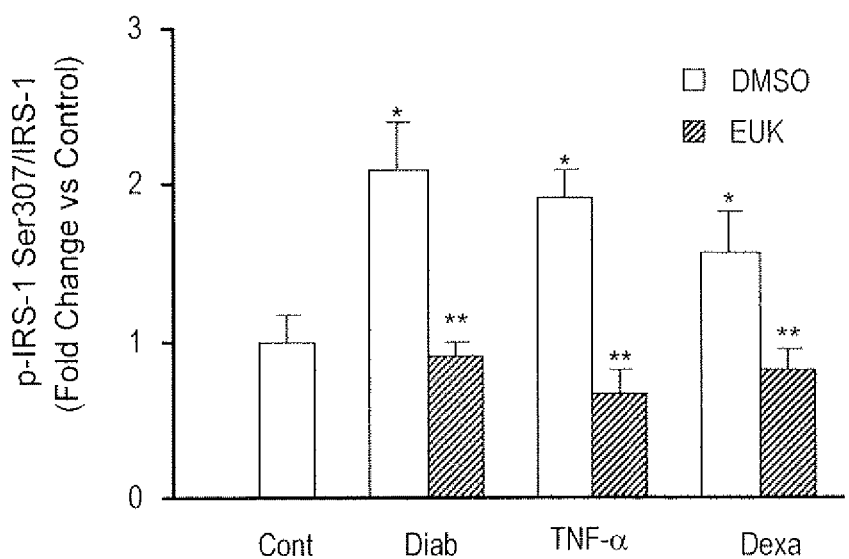
FIG. 2A is a chart showing that phosphorylation of IRS-1 at Ser307, which negatively regulates PI3K activity, is elevated in diabetic, TNF-α-, or dexamethasone-exposed cells, but that EUK-134 diminishes Ser307 phosphorylation to levels comparable to the basal level in normal fibroblasts.

Example 2 represents a study of the augmented ROS/JNK/IRS-1 Serine 307 axis in fibroblasts with phenotypic features of diabetes and hypercortisolemia. The above-described impairment in the IRS-1/PI3K/Akt signaling cascade in response to IGF-I prompted the investigation of the underlying mechanism of this phenomenon. Initially the phosphorylation status of serine residues of IRS-1, in particular p-Ser (307), was determined. IRS-1 p-Ser (307) serves as a negative feedback regulator by ablating the ability of IRS-1 to activate PI3K-dependent pathways. Data revealed that fibroblasts with diabetic and hypercortisolemic phenotypes exhibit higher levels of IRS-1 p-Ser (307) when compared to corresponding normal control values (FIG. 2A).

Figure 2B:
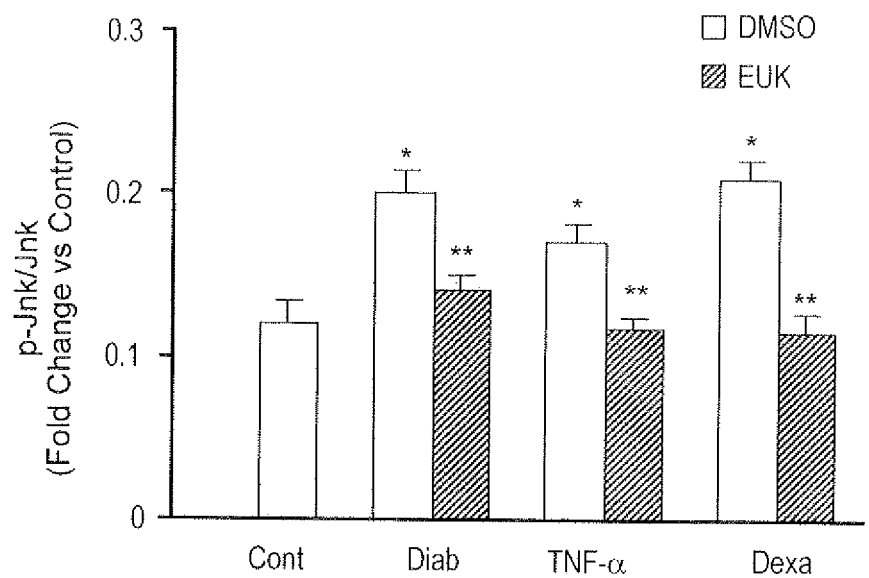
FIG. 2B is a chart showing that basal Jun N-terminal kinase (JNK) activity is higher (as measured by its phosphorylation) in diabetic, TNF-α-, or dexamethasone-exposed cells, and that EUK-134 returns its phosphorylation state to approximate levels found in normal fibroblasts.

IRS-1 contains numerous serine/threonine phosphorylation sites in amino acid sequence motifs, including Ser (307) assessed in the present study. This amino acid is potentially recognized by different kinases including the ROS-sensitive JNK. Accordingly, the ratio of p-JNK/JNK, an indicator of the activity of this MAPK-kinase-based enzyme, was determined using a FAC ELISA kit (Active Motif). The ratio was found to be enhanced in each of the models of IGF-1 resistance (FIG. 2B).

Figure 2C:
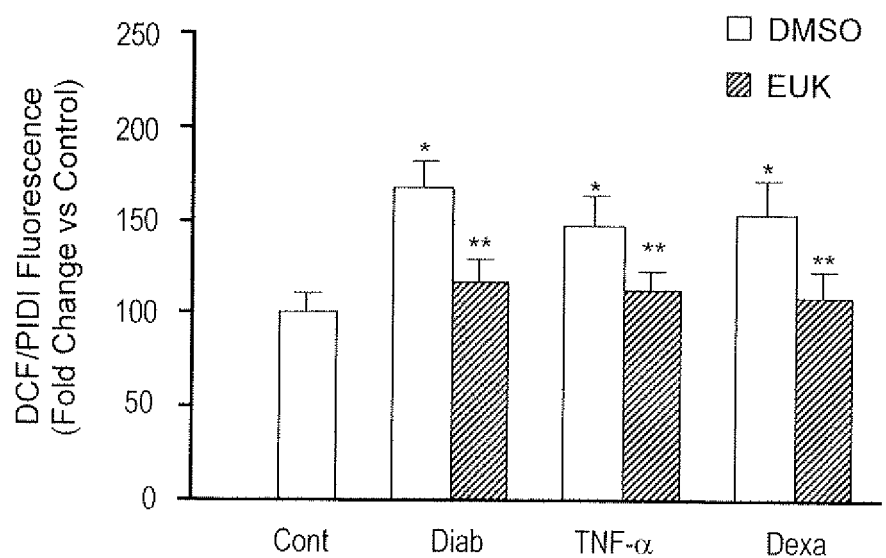
FIG. 2C is a chart showing that reactive oxygen species (ROS) are elevated in diabetic, TNF-α-, or dexamethasone-exposed cells, and that EUK-134 approximately restores normal ROS levels in these cells.
Figure 2D:
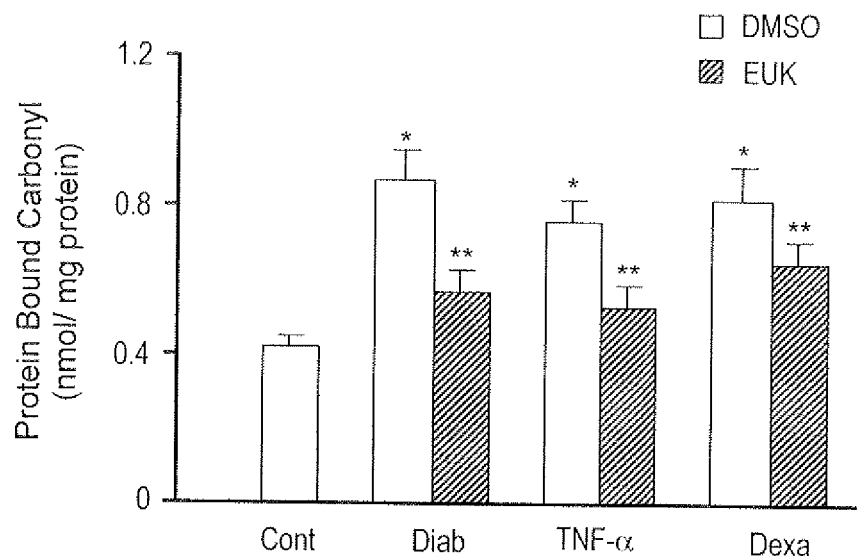
FIG. 2D is a chart showing that carbonylated protein accumulation (a marker of oxidative stress) is elevated in diabetic, TNF-α-, or dexamethasone-exposed cells versus normal control cells, and that protein carbonylation is returned to approximately normal by exposure to EUK-134.

Next it was examined whether a common mechanism underlies the activation of the JNK/IRS-1 p-Ser (307) during diabetes and hypercortisolemia, with a focus on reactive oxygen species (ROS), which are by-products of mitochondrial respiration and enzymatic oxidases. ROS levels in the current study were assessed by determining oxidation of the redox-sensitive dye DCF-DA. This probe is converted into a fluorescent product (DCF) upon reaction with $H_2O_2$, hydroxyl radical, nitric oxide, or peroxynitrite. The resulting ROS signal normalized to total cell number was markedly elevated as a function of diabetes and hypercortisolemia (FIG. 2C). Moreover, protein carbonyl levels, a marker of cumulative oxidative stress, were likewise increased in these disease states (FIG. 2D).

Example 3

Example 3 represents a study of attenuation in IGF-1-induced enhancement of collagen synthesis and cell proliferation, migration and contraction in fibroblasts with phenotypic features of diabetes and hypercortisolemia. To investigate the mechanistic basis underlying the contribution of oxidative stress-induced IGF-I resistance to impaired tissue repair mechanism during diabetes and hypercortisolemia, dermal fibroblasts exhibiting the aforementioned pathogenetic features were cultured to study key indices essential for wound healing including collagen production, cell proliferation, migration and contraction.

Figure 3A:
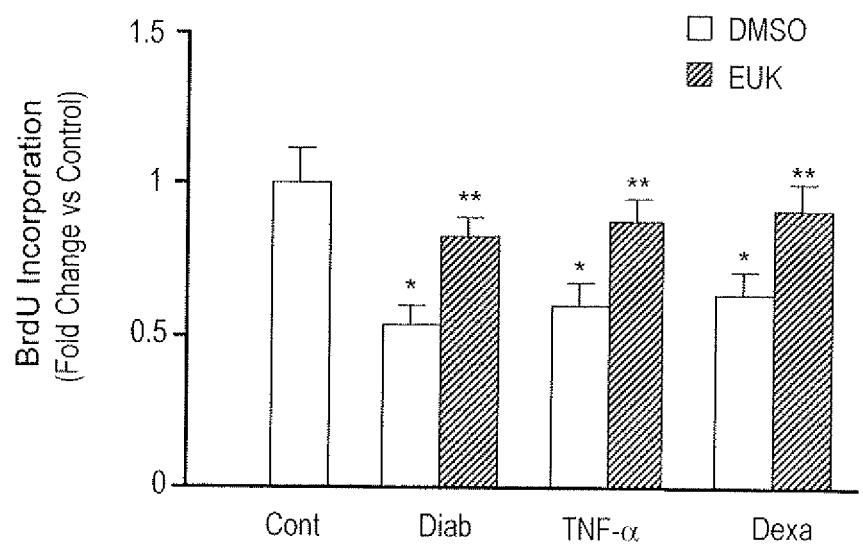
FIG. 3A is a chart showing that cell replication in isolated fibroblasts is reduced by diabetes or TNF-α or dexamethasone exposure, but that FIG. 3B is a chart showing that proline uptake, a measure of collagen synthesis, is attenuated in diabetic, TNF-α-, or dexamethasone-exposed cells, but that EUK-134 exposure returns it to approximately control levels.

A BrdU cell proliferation assay revealed that treatment of control fibroblasts with IGF-1 (50 ng/ml) for 24 hours caused a ~5-fold increase in BrdU incorporation compared with the medium only control (FIG. 3A). This action of IGF-1 in inducing DNA synthesis was reduced in diabetic and hypercortisolemic fibroblasts by about 46%, and 36%, respectively (FIG. 3A).

Figure 3B:
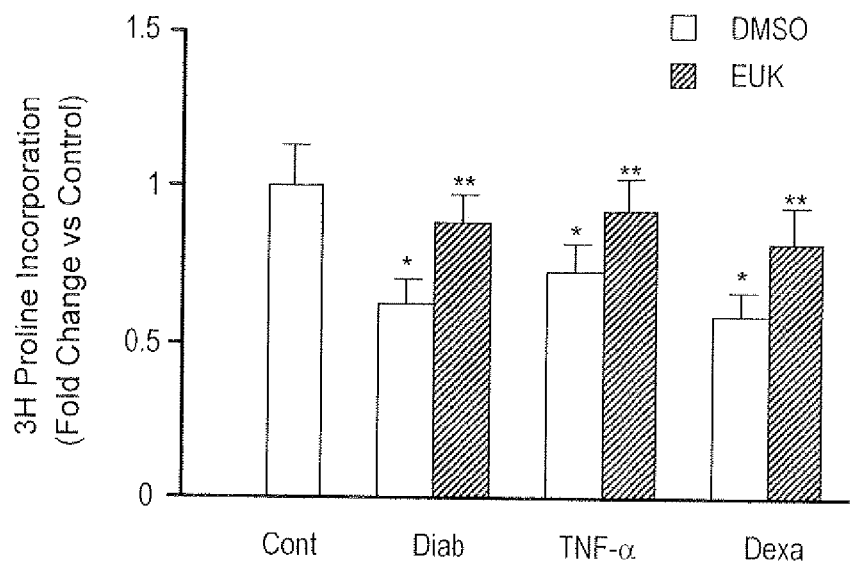
FIG. 3C is a graph showing that collagen mRNA synthesis is attenuated in diabetic, TNF-α-, or dexamethasone-exposed cells, but that EUK-134 exposure returns it to approximately control levels.
FIG. 3D is a chart showing that diabetic, TNF-α-, or dexamethasone-exposed cells show decreased contractility in a collagen gel assay, but that EUK-134 exposure partially restores this contractility to control levels.
FIG. 3E is a chart showing the rate of migration of normal control fibroblasts as well as diabetic, TNF-α-exposed, or dexamethasone-exposed cells, including treatment with IGF-1 or IGF-1 and EUK-134, measured in an artificial wounding assay.
Figure 3C:
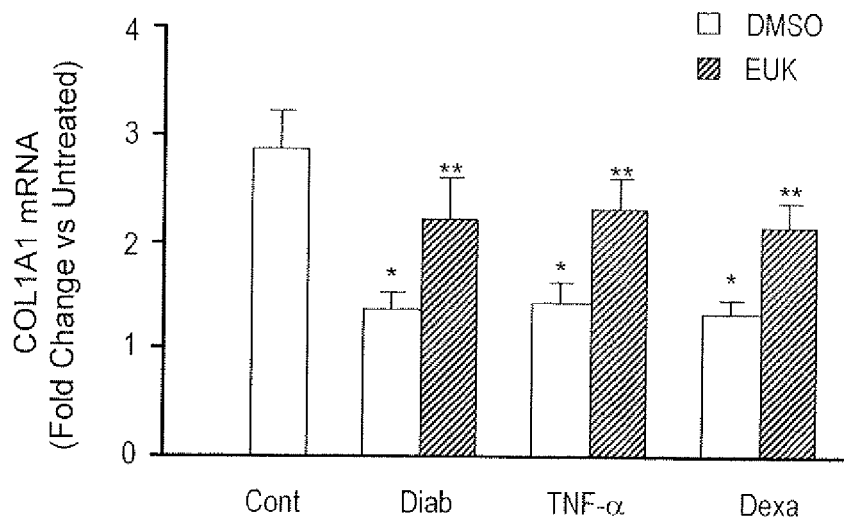

A radio-labeled proline uptake assay was used to study the impact of IGF-1 on collagen synthesis in fibroblasts of different models of oxidative stress-induced IGF-1 resistance. The data revealed that in control fibroblasts, IGF-1 increased collagen synthesis by about 63%, a phenomenon which was markedly impaired in fibroblasts with diabetic and hypercortisolemic phenotypes (FIG. 3B). Consistent with these results, a TaqMan real time PCR demonstrated that the increase in COL1A1 mRNA expression by IGF-1 was also suppressed in these cells (FIG. 3C).

Figure 3D:
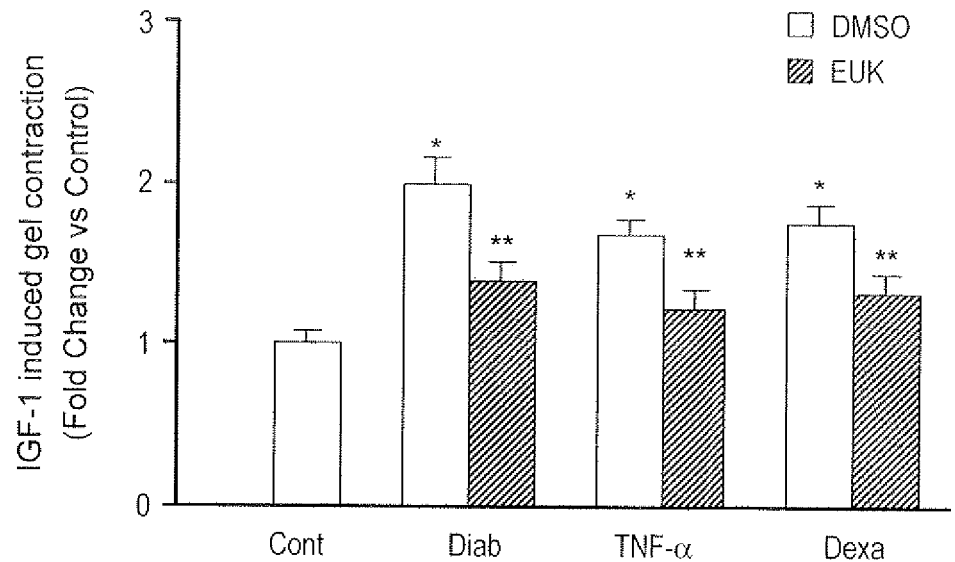
Figure 3E:
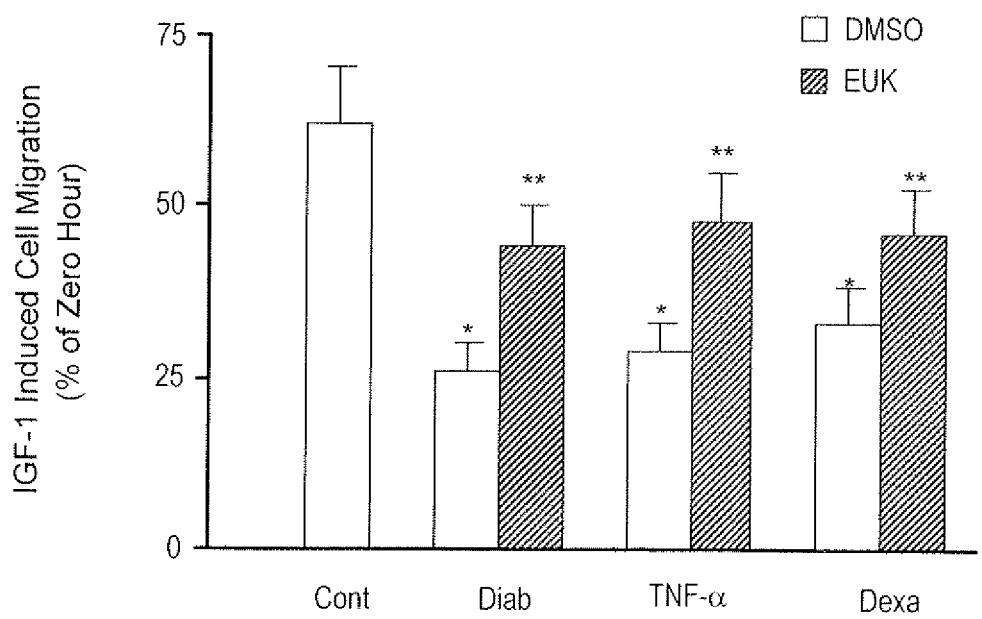

The ability of fibroblasts to migrate in response to IGF-I in each of our models of oxidative stress-induced IGF-1 resistance was also evaluated. A linear scratch was made in a fibroblast monolayer reaching confluence using a pipette tip, and fibroblast migration into the wounded area in the presence or absence of IGF-I was monitored over 24 hours, IGF-1-induced migration in dermal rat fibroblasts was markedly reduced as a function of diabetes and hypercortisolemia (FIG. 3E). It is worthy of note that the aforementioned phenomenon was associated with an attenuated ability of these cells to contract a floating collagen gel matrix following IGF-I administration (FIG. 3D).

Example 4

Example 4 represents a study of how TNF-α treated fibroblasts recapitulate the hypercortisolemic features of HSOS, IGF-1 resistance and impaired wound healing. The above data clearly indicate that HSOS, IGF-1 resistance and impaired wound healing are characteristic features of diabetes and dexamethasone-induced hypercortisolemia. Dexamethasone signals through a nuclear hormone receptor and is known for its anti-inflammatory effect, while TNF-α, a proinflammatory cytokine exerting an effect through a cytokine membrane receptor, has also been associated with insulin resistance. The current study shows evidence for IGF-1 resistance (FIG. 1A-E), HSOS (FIGS. 2C and D) and impaired wound healing (FIG. 3A-E) in control fibroblasts exposed chronically to TNF-α. The above data allow some predictions: First, that a clinical condition associated with IGF-1 resistance and impaired wound healing may also show evidence of increased ROS levels, and additionally, that conditions which elicit HSOS (e.g., diabetes, hypercortisolemia, inflammation) would be predicted to cause IGF-1 resistance and impaired wound healing.

Example 5

Example 5 represents a study of how ROS suppressors ameliorate oxidative stress-induced IGF-1 resistance and impaired wound healing during diabetes, inflammation and hypercortisolemia. To assess whether a cause and effect relationship exists between ROS and IGF-I resistance/impaired wound healing, the ROS suppressors LA and EUK-134 were administered to fibroblasts exposed to the various conditions. EUK-134 is derived from a compound with SOD activity that has been modified to obtain a strong catalase activity and it diffuses freely through the plasma membrane, while LA exhibits dual effects in which it scavenges ROS and enhances the expression of endogenous antioxidant enzymes. The data collected in these studies (only shown for EUK) clearly demonstrate that these antioxidants are able to lessen the HSOS (FIGS. 2C and D) and to correct the common defect in IGF-1 signaling (FIG. 1A-E, FIGS. 2A and B) in fibroblasts with diabetic, inflammatory or hypercortisolemia phenotypes. Moreover, this treatment also ameliorates in the aforementioned disease states the impairment in key fibroblast functions essential for wound healing including collagen synthesis, and cell proliferation, migration and contraction (FIG. 3A-E).

Example 6

Example 6 represents a study of the diminution of IGF-1 effects on glucose disposal and cutaneous wound healing during diabetes and hypercortisolemia. This study was intended to extend the above described observations from cellular levels to in viva models of excisional wounds and IGF-1 resistance. Initial data confirmed that diabetic and hypercortisolemic animals exhibited a marked increase in fasting plasma insulin, free fatty acid and glucose (only in GK rats) levels when compared to corresponding control values (Table 1).

Figure 4A:
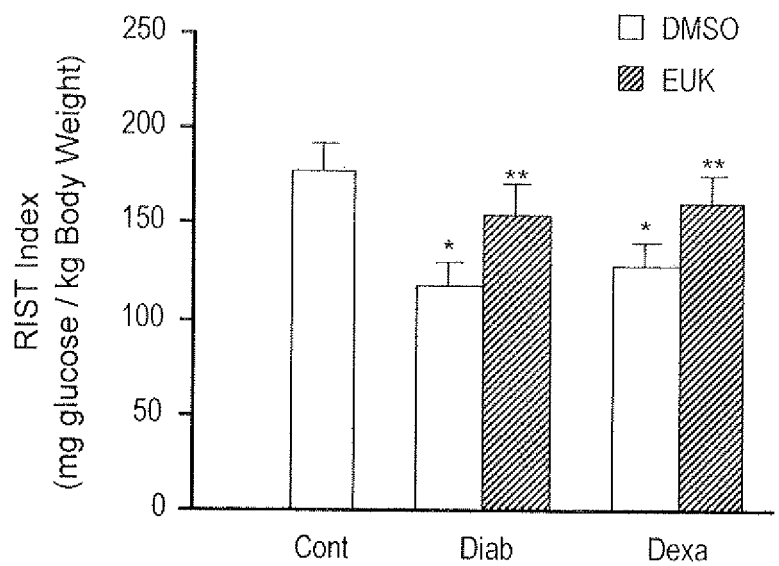
FIG. 4A is a chart showing the results of a rapid insulin sensitivity assay using IGF-1 instead of insulin for normal control rats, diabetic rats, and rats treated with dexamethasone.

Next, the RIST was used in the assessment of IGF-1 sensitivity (e.g., total amount of glucose, mg/kg body weight needed to maintain euglycemia following IGF-1 infusion) whereas the rate of healing was evaluated using a 7-day full-thickness dermal wound. Our data revealed that IGF-1 sensitivity was markedly reduced as a function of diabetes and hypercortisolemia (FIG. 4A). For example, both diabetes and hypercortisolemia induced similar reduction in IGF-1 sensitivity. While untreated rats metabolized 175 mg glucose per kg in response to a bolus injection of 50 mU of IGF-1, rats with diabetic complications or suffering from chemically-induced hypercortisolemia were only able to metabolize about 125 mg glucose per kg body weight, about a 25% to 35% reduction. Chronic administration of lipoic acid or EUK-134 improved the glucose metabolism of diabetic/hypercortisolemic rats in response to a bolus injection of IGF-1 by about 20%.

Figure 4B:
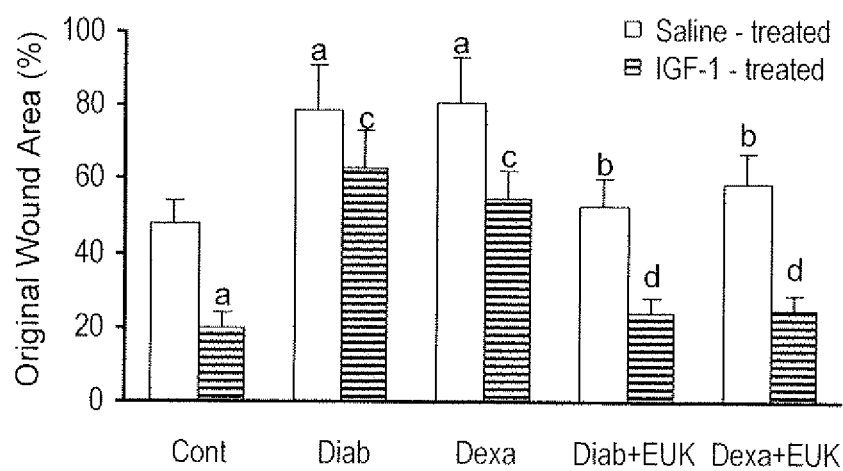
FIG. 4B is a chart showing that wounds induced on diabetic or dexamethasone-treated rats healed more slowly than on control rats, but that treatment with EUK-134- and/or IGF-1 caused diabetic rat wounds to heal as rapidly as those on control rats.

Corresponding to the RIST assessments, the in vivo wound healing studies showed that the 7-day diabetic and hypercortisolemic wounds were larger than matching control values (FIGS. 4B and C). IGF-I-based therapy involving IGF-I/IG-FBP-1 at a ratio of 5:1 reduced control, diabetic and hypercortisolemic wound sizes by about 41%, 12% and 17%, respectively (FIGS. 4B and C). Administration of EUK-134 or □-lipoic acid to diabetic/hypercortisolemic rat wounds resulted in healing rates that are statistically indistinguishable from control rat wounds treated with IGF-1 alone. Interestingly, the above abnormalities regarding lipid and carbohydrate profiles as well as the impairment in systemic and wound-based IGF-1 actions were ameliorated in response to chronic treatment with the ROS suppressors EUK-134 and LA (Table 1 and FIG. 4A-C, data only shown for EUK-134).

TABLE 1

Effect of EUK 134 on diabetic and hypercortisolemic rats

| Parameters | Cont | Diab | Dexa | Diab + EUK | Dexa + EUK |
|---|---|---|---|---|---|
| BW (g) | 242 ± 14 | 237 ± 12 | 233 ± 10 | 245 ± 17 | 240 ± 15 |
| FFA (μM) | 283 ± 19 | 635 ± 22* | 706 ± 25* | 353 ± 18** | 327 ± 16** |
| FBG (mg/dl) | 83 ± 10 | 137 ± 13* | 78 ± 9 | 122 ± 18 | 81 ± 12 |
| FPI (ng/ml) | 0.52 ± 0.04 | 0.92 ± 0.08* | 0.78 ± 0.061* | 0.66 ± 0.05** | 0.58 ± 0.052** |

Values are the mean ± S.E.M.
Abbreviations: BW: Body weight; FFA: Free fatty acid; FBG: Fasting blood glucose; FPI: Fasting plasma insulin
*Significantly different from corresponding control values at $P \leq 0.05$
**Significantly different from corresponding D or HC values at $P \leq 0.05$ It is to be understood that the present invention is not limited to the embodiments described above, but encompasses any and all embodiments within the scope of the following claims.

We claim:

1. A method of diagnosing a risk of oxidative stress-impaired wound healing in a subject by testing for oxidative stress, comprising the steps of:
    detecting IGF-1 resistance in said subject, wherein detection of IGF-1 resistance indicates an increased risk of oxidative stress-impaired wound healing in said subject, wherein identifying IGF-1 resistance in a subject comprises the steps of:
        administering to the subject a dose of IGF-1 to modulate said subject's glucose metabolism;
        comparing said subject's measured glucose metabolism in response to the dose of IGF-1 to a known standard response to a similar dose of IGF-1;
        if said subject's measured glucose metabolism is below the known standard response to a similar dose of IGF-1, administering to the subject a dose of an antioxidant, wherein the antioxidant is EUK-134;
        repeating the step of administering to the subject a dose of IGF-1 effective to modulate said subject's glucose metabolism;
        repeating the step of measuring said subject's glucose metabolism in response to the dose of IGF-1; and
        comparing said subject's glucose metabolism in response to IGF-1 before administering the antioxidant with said subject's glucose metabolism in response to IGF-1 after administering the antioxidant;
        wherein a determination that the antioxidant increases said subject's glucose metabolism in response to the dose of IGF-1 indicates that said subject suffers from oxidative stress.

2. A method of diagnosing a risk of oxidative stress-impaired wound healing in a subject by testing for oxidative stress, comprising the steps of,
    Detecting IGF-1 resistance in said subject, wherein detection of IGF-1 resistance indicates an increased risk of oxidative stress-impaired wound healing in said subject, wherein identifying IGF-1 resistance in a subject comprises the steps of:
        administering to the subject a dose of IGF-1 to modulate said subject's glucose metabolism;
        comparing said subject's measured glucose metabolism in response to the dose of IGF-1 to a known standard response to a similar dose of IGF-1;
        if said subject's measured glucose metabolism is below the known standard response to a similar dose of IGF-1, administering to the subject a dose of an antioxidant, wherein the antioxidant is $\alpha$-lipoic acid;
        repeating the step of administering to the subject a dose of IGF-1 to modulate said subject's glucose metabolism;
        repeating the step of measuring said subject's glucose metabolism in response to the dose of IGF-1; and
        comparing said subject's measured glucose metabolism in response IGF-1 before administering the antioxidant with said subject's glucose metabolism in response to IGF-1 after administering the antioxidant;
        wherein a determination that the antioxidant increases said subject's glucose metabolism in response to the dose of IGF-1 indicates that the subject suffers from oxidative stress.

* * * * *